United States Patent [19]

Markussen et al.

[11] Patent Number: 5,008,241

[45] Date of Patent: * Apr. 16, 1991

[54] NOVEL INSULIN PEPTIDES

[75] Inventors: Jan Markussen, Herlev; Kjeld Norris, Hellerup; Liselotte Langkjaer, Klampenborg, all of Denmark

[73] Assignee: Novo Nordisk A/S, Bagsvaerd, Denmark

[*] Notice: The portion of the term of this patent subsequent to Aug. 7, 2007 has been disclaimed.

[21] Appl. No.: 424,503

[22] Filed: Oct. 20, 1989

Related U.S. Application Data

[63] Continuation of Ser. No. 75,550, Jul. 20, 1987, abandoned, which is a continuation-in-part of Ser. No. 838,472, Mar. 11, 1986, abandoned.

[30] Foreign Application Priority Data

| Mar. 12, 1985 | [DK] | Denmark | 1135/85 |
| Mar. 10, 1986 | [DK] | Denmark | 1070/86 |
| Jul. 21, 1986 | [DK] | Denmark | 3470/86 |
| Feb. 25, 1987 | [DK] | Denmark | 0948/87 |

[51] Int. Cl.$^5$ .................. A61K 37/26; C07K 7/40; C07K 7/42
[52] U.S. Cl. ................................ 514/3; 514/4; 514/866; 530/303; 530/304
[58] Field of Search ............... 530/303, 304; 514/3, 514/4, 866

[56] References Cited

U.S. PATENT DOCUMENTS

| 3,364,116 | 1/1968 | Bodanszky et al. | 530/303 |
| 3,528,960 | 9/1970 | Haas | 530/303 |
| 3,883,496 | 5/1975 | Geiger | 530/303 |
| 4,421,685 | 12/1983 | Chance et al. | 530/303 |
| 4,608,364 | 8/1986 | Grau | 514/3 |
| 4,737,487 | 4/1988 | Watts et al. | 530/328 |

FOREIGN PATENT DOCUMENTS

| 0163529 | 12/1985 | European Pat. Off. |
| 0194864 | 9/1986 | European Pat. Off. |

OTHER PUBLICATIONS

Rudinger, Peptide Hormones, Parsons (Ed.) U. Park Press, Baltimore, pp. 1-7 (1976).
Brandenburg et al., Int. Congr. Ser. Excerpta Med. 413 (Diabetes) pp. 163-168 (1977).
Norris et al., Nucleic Acids Research, vol. 11, No. 15, pp. 5103-5112 (1983).
Lehninger, Principles of Biochemistry, Worth Publishers, Inc., New York, pp. 95-117 (1982).
Markussen et al., Protein Engineering, vol. 1, No. 3, pp. 205-213, 215-223 (1987).
Markussen et al., Protein Engineering, vol. 2, No. 2, pp. 157-165 (1988).

*Primary Examiner*—John Doll
*Assistant Examiner*—Christina Chan
*Attorney, Agent, or Firm*—Morris Fidelman; Franklin D. Wolffe

[57] ABSTRACT

Insulin analogs characterized by amino acid residue at A21 other than Asn, with a resulting improvement in stability of insulin solutions at acid pH levels. Some insulin analogs may also have amino acid residue changes elsewhere so that these insulin analogs exhibit at least about one charge more than human insulin at a pH value of 7, with preferred substitutions being made for the glutamic acid residues at A4, A17, B13, B21 and/or a basic amino acid residue being substituted at B27. Also contemplated is optional blocking the C-terminal carboxyl group of the B-chain with an amido or ester residue.

10 Claims, No Drawings

NOVEL INSULIN PEPTIDES

This application is a continuation of Ser. No. 075,550 filed Jul. 20, 1987, now abandoned, which in turn is a continuation-in-part of Ser. No. 838,472, filed Mar. 11, 1986, now abandoned.

BACKGROUND OF THIS INVENTION

The present invention relates to novel, stabilized insulin analogs and, in a preferred embodiment, to novel injectable solutions having prolonged insulin action.

In the treatment of diabetes mellitus, many varieties of insulin preparations have been suggested and used. Some of the preparations are fast acting and other preparations have more or less prolonged actions. Such a prolonged action may be obtained by administering the insulin as a suspension of insulin crystals. The crystalline preparations can be obtained by crystallization of insulin in the presence of zinc (such as LENTE ™, see Schlichtkrull: Insulin Crystals, Chemical and Biological Studies on Insulin Crystals and Insulin Zinc Suspensions, Munksgaard, 1958) or by crystallization of insulin in the presence of zinc and protamine (such as NPH-insulin, see Rep.Steno Mem.Hosp. 1 (1946), 60).

Acid solution of insulin have been used earlier, both as short-acting preparations and as long-acting preparations containing protamine and zinc. However, the chemical stability of insulin at pH-values below 4.5 is low, as formation of desamidoinsulins (Sundby, F., J.Biol.Chem. 237 (1962), 3406–3411) and covalent dimers (Steiner et al, Diabetes 17 (1968), 725–736) takes place. In the pH-range 4.5–6.5, insulin precipitates. Hence, in order to make soluble short-acting insulin preparations (addition of blood-flow enhancing agent) and long-acting insulin preparations (addition of protamine and/or zinc) an insulin stable at low pH would be desirable.

It is known that during the acid ethanol extraction of mammalian insulins many dimers are formed (Steiner) and, furthermore, monodesamidoinsulins are formed under acid conditions (Sundby).

One disadvantage in the use of the known suspensions of zinc insulin crystals or of zinc protamine insulin is the necessity of shaking the vial in order to ensure that the correct amount of insulin is being injected and to ensure that the concentration of insulin in the vial remains constant throughout its use. In PENEILL ™ cartridges where air must be absent, prolonged acting insulin suspensions require the incorporation of a solid body in the cartridge to enable agitation. The shaking of insulin suspensions and insulin solutions with air is in itself an undesirable process, as insulin has a tendency to denature under formation of fibrills at water-air interfaces. Consequently, solutions of insulins with prolonged action are desirable.

Solutions of insulin derivatives having a prolonged action were obtained from insulin that had been modified in its amino groups by reaction with phenylisocyanate (so-called Isoinsulin, see Hallas-Moeller: Chemical and Biological Insulin Studies based upon the Reaction between Insulin and Phenylisocyanate, Copenhagen 1945). Similarly, A1,B29-di-Boc substituted insulin (Boc designates tertiary butyloxycarbonyl) was reported to show a prolonged insulin action after subcutaneous administration (see Geiger & Enzmann in: Proinsulin, Insulin, C-peptide; Proceedings of the Symposium on Proinsulin, Insulin and C-Peptide, Tokushima 1978; Amsterdam Oxford 1979, 306–310). The A1,B29-di-Boc substituted insulin was found to exhibit a too slightly prolonged action to be clinically useful.

Solutions of unmodified insulins require large amounts of zinc ions (for example, 0.4–1 mg/U insulin) in order to exhibit a prolonged action (see J.Pharmacol. 55 (1935), 206). Injection of such large doses of zinc ions will probably cause pain and such solutions have, therefore, never been used in therapy.

The isoelectric point of insulin is about 5.5 and attempts have been made to decrease the solubility of insulin derivatives at neutral pH by shifting the isoelectric point upwards, for example, through additions, in the N-terminus of the B-chain, of basic amino acids like lysine or arginine (see, for example, German *Offenlegungsschrift* No. 2,042,299) or with the basic dipeptide arginyl-arginine (see Geiger & Enzmann cited above). However, near its isoelectric point the solubility of $Arg^{B(-1)}-Arg^{B0}$ insulin was much higher than that of the parent insulin.

Japanese patent application No. 55-144032 relates to analogues to human insulin wherein the B30-amino acid has been replaced by an amino acid having at least five carbon atoms, and amides and esters thereof. These insulin analogues were to be used in patients who had developed antibodies against mammalian insulins. In the Japanese patent application, six specific compounds are described, none of which were stated to have prolonged action. No specific injectable preparations are described in the Japanese patent application.

European patent application No. 84108442 relates to insulin analogues wherein a basic, organic group is attached to the B30-amino acid thereby introducing a positive charge at neutral pH. In these analogues, the B30-amino acid is neutral and, preferably, threonine as in human insulin. German patent application No. 3,327,709 relates to a suspension of crystals of the derivatives described in the above-noted European patent application as well as an aromatic hydroxy compound. German patent application No. 3,326,473 relates to a medicament containing a mixture of insulin compounds, of which at least one is described in the above-noted European patent application.

One object of this invention is to prepare insulin derivatives with improved properties.

A second object of this invention is to prepare insulin solutions having an improved stability.

A third object of this invention is to prepare insulin preparations with no or low immunogenic action.

A fourth object of this invention is to prepare insulin analogs which are dissolved at pH values below about 5.8.

The present invention arose within the context of prolonged action insulin described above but is not limited thereto.

Acid insulin solutions, a form that many years ago represented the only insulin form employed in diabetes therapy, are relatively unstable (with substantial deamidation at A-21 taking place). Substituting a more stable amino acid residue for $Asn^{A21}$ improves the stability of the insulin molecule at pH levels lower than its isoelectric point. Solutions of the A-21 substituted insulin analogs of this invention are characterized by improved stability at acid pH levels.

BRIEF STATEMENT OF THIS INVENTION

The present invention comprises novel analogs of insulin that differ from human insulin in that the C-terminal asparagine residue of the A-chain, $Asn^{A21}$, is substituted by any other naturally occurring amino acid, which can be coded for by nucleotide sequences, or by homoserine. Also optionally, but preferably:

(a) an amide or ester residue on the C-terminal carboxyl group of the B-chain is present, and (b) the insulin analog has at least one charge more than human insulin at a pH value at 7, preferably not more than 4 charges more than human insulin at a pH value of 7.

The optional increase in charge is achieved by appropriate substitution of a more basic amino acid residue for one or more of the amino acid residues in human insulin and, if desired, by the blocking of the carboxylic group in the B30 amino acid.

Thus, the insulin analogs of this invention comprise insulin analogs characterized by an A-21 residue which preferably is selected from the group consisting of Glu, Asp, Lys, Arg, His, Val, Gln, Ile, Phe, Tyr, Met, Gly, Ser, Thr, Ala, Leu, Trp and hSer.

One preferred set of A21 substituents are the acidic residues of Glu and Asp, the latter being the more preferred.

A second set of preferred A21 substituents are the basic residues of Lys, Arg and His, histidine being the more preferred.

A third set of preferred A21 substituents are the neutral residues of valine, glutamine, isoleucine, phenylalanine, tyrosine or methionine and more preferably glycine, serine, threonine, alanine or homoserine.

In addition, preferred insulin analogs of interest to practice of this invention are characterizable as follows: One or more of the four glutamic acid residues at A4, A17, B13 and B21 are replaced by another naturally occurring neutral amino acid residue, preferably a glutamine residue; and/or the threonine residue at B27 is instead a naturally occurring basic amino acid residue, preferably an L-arginine or L-lysine residue; and/or the threonine residue at B30 is replaced by one or two basic amino acid residues, one being preferred; and/or the C-terminal carboxylic group in the B chain may be protected. For example, desirably by —NH$_2$.

This invention also comprises solutions of the insulin analogs, optionally containing a controlled level of zinc ions therein within a concentration of 5 μg to 200 μg per ml. The degree of prolongation of insulin action is enhanced and controlled by the addition of zinc ions.

DETAILED PRACTICE OF THIS INVENTION

It has surprisingly been found that injectable solutions with improved stability, most of which also have a surprisingly combined short and prolonged insulin action, can be made using, as the active ingredient, a single insulin derivative having the general formula I quences, X represents an L-threonine, L-arginine or L-lysine residue, Y and Z are the same or different and each represent an amino acid residue wherein any side chain amino group may be acylated and wherein any side chain hydroxy group may be alkylated, m, n and p are the same or different and each represent zero or one, R represents an amido or ester residue which blocks the C-terminal carboxyl group of the B-chain, and W represents an amino acid residue other than asparagine, with the proviso that if all four amino acid residues $E^1$, $E^2$, $E^3$ and $E^4$ are glutamic acid residues, X is Thr, and —$Y_m$—$Z_n$—$R^p$ is —Ala, then W is different from aspartic acid.

Furthermore, it is surprising that the compounds of this invention have a low formation of dimers. Mammalian insulin contains Asn in the A21 position. Therefore, it is surprising that the compounds of this invention have a satisfactory insulin activity.

Preferably, substitution is made at one or more of the 7 amino acid residues $E^1$, $E^2$, $E^3$, $E^4$, X, Y and Z and the group R causing the compound of formula I to have at least one charge more than human insulin at a pH value of 7.

The novel insulin analogs have the further advantages:

(1) The formation of the immunogen dimer, i.e. covalently linked insulin molecules linked either through the two A-chains, (AA) dimer, or through one A-chain and one B-chain, (AB) dimer, (Helbig, H. J., Deutsche Wollforschungsinstitut, dissertation, 1976), is substantially decreased. A chromatographic fraction of crude porcine insulin, the b-component, containing the dimers was shown to be immunogenic in rabbits (Schlichtkrull et al., Horm.Metab.Res. Suppl. 5 (1974) 134–143).

(2) The stability of the novel insulin derivatives is so high that it will probably be acceptable to store preparations containing these novel insulin derivatives at room temperature for a long period of time. This will be a major advantage for the patient.

(3) It will be possible to prepare dissolved preparations containing the novel insulin derivatives at pH values from about 2 to about 5.8.

(4) It will be possible to prepare preparations containing the novel insulin derivatives which, at pH values of about 3, have a substantially improved chemical stability.

(5) It will be possible to prepare soluble, rapidly acting preparations containing the novel insulin derivatives by the addition of compounds which enhance the absorption.

(6) It will be possible to prepare soluble, retarded preparations containing the novel insulin derivatives by the addition of zinc and/or protamine to acid solutions,

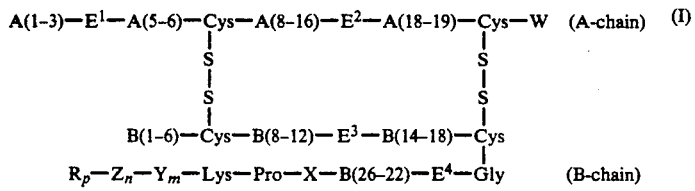

wherein the letters A and B followed by figures in parentheses designate the peptide fragments of the A- and B-chains, respectively, indicated by the figures in parentheses, $E^1$, $E^2$, $E^3$ and $E^4$ are the same or different each representing a glutamic acid residue or a neutral amino acid residue which can be coded for by nucleotide sei.e. solutions having a pH value in the range from about 2.5 to about 5.8.

(7) It will be possible to prepare preparations containing the novel insulin derivatives having different absorption profiles.

A subgroup of compounds of formula I is novel compounds having the general formula I wherein R represents an amido residue.

If, compared with human insulin at a pH value of 7, a change in charge is desired in the insulin analogs of this invention, it is obtained by substituting the threonine residue in the B27-position with an arginine or lysine residue and/or by substituting one or more of the four glutamic acid residues in the A4-, A17-, B13-, and B21-position with a neutral amino acid residue, preferably with a glutamine residue. In addition, the C-terminal carboxyl group of the B-chain may be blocked by an ester group or amide group, thereby eliminating the negative charge of this B-30 carboxyl group. Furthermore, a positive charge may be introduced by presence of a basic amino acid residue in the B30- and/or B31-position.

Since the preferred compounds of formula I can be applied in the clinic as solutions having a prolonged action, a decline in immunogenicity as compared to the commonly used suspensions of porcine or human insulins may occur.

The degree of prolongation depends on the concentration of zinc ions in the preparation.

Major parameters that control the degree of prolongation of the insulin effect are the concentration of zinc and the choice of the compound of formula I. The range for the preferred zinc content extends from 0 to about 2 mg/ml, preferably from 0 to 200 $\mu$g/ml zinc with substitution in the B13 and/or B27 position and from about 20 to 200 $\mu$g/ml with other analogs in a preparation containing 240 nmole of a compound of formula I per ml. Using other concentrations of the compound of formula I, the content of zinc is to be adjusted correspondingly.

The prolonged action of solutions of compounds of formula I in the presence of zinc ions is ascribed to the low solubility of such compounds at neutral pH.

The pH of the injectable solution of this invention should preferably be below the physiological pH, the upper limit being the pH where precipitation occurs. At the physiological pH value, compounds of formula I of this invention have a low solubility. Stable solutions containing about 240 nmole/ml of compounds of formula I have been obtained at pH about 5.5. The upper limit depends upon the constituents of the solution, i.e. isotonic agent, preservative and zinc concentration, and upon the choice of compound of formula I. There is no lower pH limit of the solutions and the chemical stability of the compounds of formula I is high, even at pH 3. The preferred pH range for the injectable solutions of this invention is from about 2.5 to 5.8, more preferred being about 2.8 to 4.5.

A further aspect of this invention is that it provides improved flexibility for the patients. With two aqueous solutions, one containing a compound of formula I and the other containing a zinc salt, the patient can obtain a desired degree of prolonged action and a desired profile by mixing the two solutions appropriately. Thus, the patient has, using two stock solutions, the possibility of choosing one action and profile for the morning injection and another action and profile for the evening injection. Preferably, the zinc solution contains between about 2 $\mu$g and 20 mg zinc per ml. Alternatively, both of the stock solutions may contain zinc, either in the same or different concentrations, and/or both the stock solutions may contain a compound of formula I, either the same or different compounds.

Preferably, the injectable solutions of this invention have a strength of between about 60 and 6000 nmole of the compound of formula I per ml.

It has already been pointed out that W may be a neutral L-amino acid, for example valine, glutamine, isoleucine, leucine, phenylalanine, tyrosine, methionine or preferably glycine, serine, threonine, alanine or homoserine. W may be an acidic amino acid, viz. glutamic acid or preferably aspartic acid, or a basic amino acid, viz. lysine, arginine of preferably histidine.

The neutral amino acid ($E^1$ through $E^4$) is, for example, glycine, valine, isoleucine, leucine, phenylalanine, tyrosine, methionine or preferably asparagine, glutamine, alanine, serine or threonine.

Examples of R are ester moieties, for example, lower alkoxy, preferably methoxy, ethoxy and most preferred tertiary butoxy.

Furthermore, R can be a group of the general formula —$NR^1R^2$ wherein $R^1$ and $R^2$ are the same or different and each represents hydrogen or lower alkyl. Hereinafter the term "lower" designates that the group in question contains less than 7 carbon atoms, preferably less than 5 carbon atoms. In a preferred embodiment of this invention, R is —$NH_2$. Furthermore, R may be a lactam residue which preferably contains less than 8 atoms in the lactam ring, for example a lactam of a diaminocarboxylic acid.

In a preferred embodiment of this invention, R is uncharged.

According to one preferred embodiment of this invention, the amino acid residues designated Y and Z are residues from L-amino acids which are coded for by nucleotide sequences.

Any side chain amino group in the amino acid residues designated Y and Z may be acylated by an acid containing from 2 to 18 carbon atoms, preferably a fatty acid containing from 6 to 18 carbon atoms, for example, lauric acid. Thus, —$Y_m$—$Z_n$—$R_p$ may be —Lys(Lau)-$NH_2$.

Examples of preferred alkylated hydroxy groups are methoxy, ethoxy and tertiary butoxy.

In one group of preferred compounds of formula I Y and/or Z is a basic amino acid residue wherein the side chain amino group optionally is acylated (m=1).

In another group of preferred compounds of formula I n is zero and Y is a basic amino acid residue (m=1).

In a further group of preferred compounds of formula I Y and Z are both basic amino acid residues (m=1, n=1).

Another preferred embodiment of this invention is preparations containing a compound of formula I wherein El, E2, $E^3$ and/or $E^4$ is a glutamine residue, and/or X is Lys or Arg, and W is Gly, Ser, Thr, Ala, His, Asp or hSer, and within this subclass of compounds of formula I, a further preferred embodiment is preparations containing a compound of formula I wherein the group —$Y_m$—$Z_n$—$R_p$—Thr—NH or —Lys—$NH_2$.

Specific preferred compounds of formula I are each of the following:

Gly$^{A21}$,Lys$^{B27}$,Thr$^{B30}$—$NH_2$ human insulin,
Ser$^{A21}$,Lys$^{B27}$,Thr$^{B30}$—$NH_2$ human insulin,
Thr$^{A21}$,Lys$^{B27}$,Thr$^{B30}$—$NH_2$ human insulin,
Ala$^{A21}$,Lys$^{B27}$,Thr$^{B30}$—$NH_2$ human insulin,
His$^{A21}$,Lys$^{B27}$,Thr$^{B30}$—$NH_2$ human insulin,
Asp$^{A21}$,Lys$^{B27}$,Thr$^{B30}$—$NH_2$ human insulin,
Gly$^{A21}$,Arg$^{B27}$,Thr$^{B30}$—$NH_2$ human insulin,
Ser$^{A21}$,Arg$^{B27}$,Thr$^{B30}$—$NH_2$ human insulin,
Thr$^{A21}$,Arg$^{B27}$,Thr$^{B30}$—$NH_2$ human insulin, Ala$^{A21}$,Arg$^{B27}$,Thr$^{B30}$—NH$_2$ human insulin,
His$^{A21}$,Arg$^{B27}$,Thr$^{B30}$—NH$_2$ human insulin,
Asp$^{A21}$,Arg$^{B27}$,Thr$^{B30}$—NH$_2$ human insulin,
Gln$^{B13}$,Gly$^{A21}$,Arg$^{B27}$,Thr$^{B30}$—NH$_2$ human insulin,
Gln$^{B13}$,Ser$^{A21}$,Arg$^{B27}$,Thr$^{B30}$—NH$_2$ human insulin,
Gln$^{B13}$,Thr$^{A21}$,Arg$^{B27}$,Thr$^{B30}$—NH$_2$ human insulin,
Gln$^{B13}$,Ala$^{A21}$,Arg$^{B27}$,Thr$^{B30}$—NH$_2$ human insulin,
Gln$^{B13}$,His$^{A21}$,Arg$^{B27}$,Thr$^{B30}$—NH$_2$ human insulin,
Gln$^{B13}$,Asp$^{A21}$,Arg$^{B27}$,Thr$^{B30}$—NH$_2$ human insulin,
Gln$^{B13}$,Gly$^{A21}$,Lys$^{B27}$,Thr$^{B30}$—NH$_2$ human insulin,
Gln$^{B13}$,Ser$^{A21}$,Lys$^{B27}$,Thr$^{B30}$—NH$_2$ human insulin,
Gln$^{B13}$,Thr$^{A21}$,Lys$^{B27}$,Thr$^{B30}$—NH$_2$ human insulin,
Gln$^{B13}$,Ala$^{A21}$,Lys$^{B27}$,Thr$^{B30}$—NH$_2$ human insulin,
Gln$^{B13}$,His$^{A21}$,Lys$^{B27}$,Thr$^{B30}$—NH$_2$ human insulin and
Gln$^{B13}$,Asp$^{A21}$,Lys$^{B27}$,Thr$^{B30}$—NH$_2$ human insulin Another preferred embodiment of this invention is preparations containing a compound of formula I in which m is one, n is zero, Y is Thr, Ala or Ser, R is hydroxy, and W is Gly, Ser, Thr, Ala, His or Asp, and examples of such compounds are as follows:
Ser$^{A21}$,Lys$^{B27}$ human insulin,
Thr$^{A21}$,Lys$^{B27}$ human insulin,
Ala$^{A21}$,Lys$^{B27}$ human insulin,
His$^{A21}$,Lys$^{B27}$ human insulin,
Asp$^{A21}$,Lys$^{B27}$ human insulin,
Gly$^{A21}$,Lys$^{B27}$ human insulin,
Ser$^{A21}$,Arg$^{B27}$ human insulin,
Thr$^{A21}$,Arg$^{B27}$ human insulin,
Ala$^{A21}$,Arg$^{B27}$ human insulin,
His$^{A21}$,Arg$^{B27}$ human insulin,
Asp$^{A21}$,Arg$^{B27}$ human insulin,
Gly$^{A21}$,Arg$^{B27}$ human insulin,
Gln$^{A21}$,Ser$^{A21}$,Arg$^{B27}$ human insulin,
Gln$^{A21}$,Thr$^{A21}$,Arg$^{B27}$ human insulin,
Gln$^{A21}$,Ala$^{A21}$,Arg$^{B27}$ human insulin,
Gln$^{A21}$,His$^{A21}$,Arg$^{B27}$ human insulin,
Gln$^{A21}$,Asp$^{A21}$,Arg$^{B27}$ human insulin,
Gln$^{A21}$,Gly$^{A21}$,Arg$^{B27}$ human insulin,
Gln$^{A21}$,Ser$^{A21}$,Gln$^{B13}$ human insulin,
Gln$^{A21}$,Thr$^{A21}$,Gln$^{B13}$ human insulin,
Gln$^{A21}$,Ala$^{A21}$,Gln$^{B13}$ human insulin,
Gln$^{A21}$,His$^{A21}$,Gln$^{B13}$ human insulin,
Gln$^{A21}$,Asp$^{A21}$,Gln$^{B13}$ human insulin,
Gln$^{A21}$,Gly$^{A21}$,Gln$^{B13}$ human insulin,
Arg$^{B27}$,Ser$^{A21}$,Gln$^{B13}$ human insulin,
Arg$^{B27}$,Thr$^{A21}$,Gln$^{B13}$ human insulin,
Arg$^{B27}$,Ala$^{A21}$,Gln$^{B13}$ human insulin,
Arg$^{B27}$,His$^{A21}$,Gln$^{B13}$ human insulin,
Arg$^{B27}$,Asp$^{A21}$,Gln$^{B13}$ human insulin,
Arg$^{B27}$,Gly$^{A21}$,Gln$^{B13}$ human insulin,
Gln$^{A21}$,Ser$^{A21}$,Lys$^{B27}$ human insulin,
Gln$^{A21}$,Thr$^{A21}$,Lys$^{B27}$ human insulin,
Gln$^{A21}$,Ala$^{A21}$,Lys$^{B27}$ human insulin,
Gln$^{A21}$,His$^{A21}$,Lys$^{B27}$ human insulin,
Gln$^{A21}$,Asp$^{A21}$,Lys$^{B27}$ human insulin,
Gln$^{A21}$,Gly$^{A21}$,Lys$^{B27}$ human insulin,
Gln$^{B13}$,Ser$^{A21}$,Lys$^{B27}$ human insulin,
Gln$^{B13}$,Thr$^{A21}$,Lys$^{B27}$ human insulin,
Gln$^{B13}$,Ala$^{A21}$,Lys$^{B27}$ human insulin,
Gln$^{B13}$,His$^{A21}$,Lys$^{B27}$ human insulin,
Gln$^{B13}$,Asp$^{A21}$,Lys$^{B27}$ human insulin
Gln$^{B13}$,Gly$^{A21}$,Lys$^{B27}$ human insulin, and
Ser$^{A21}$,Arg$^{B27}$,Thr$^{B30}$—NH$_2$ human insulin.

Further examples of specific preferred compounds according to this invention are the following: GlyA21 human insulin, Ala$^{A21}$ human insulin, Ser$^{A21}$ human insulin, Thr$^{A21}$ human insulin, hSer$^{A21}$ human insulin, Gly$^{A21}$ porcine insulin, Ala$^{A21}$ porcine insulin, SerA21 porcine insulin and ThrA21 porcine insulin.

In one group of preferred compounds of formula I, $E^2$ and $E^3$ is a glutamine residue.

In another group of preferred compounds of formula I, X is an arginine or lysine residue.

In a further group of preferred compounds of formula I, W is Gly, Ser, Thr, Ala, His, Asp or hSer.

As is well known in the art, not all of the amino acid residues in human insulin are essential for the insulin action.

Indeed, porcine insulin and bovine insulin which differs from human insulin in amino acid residues have been employed to treat diabetics. Considerable species to species variations exist in the insulin molecule. Thus, many amino acid residues in the human insulin molecule may be changed without undue diminution in insulin activity, including some residues influencing the isoelectric point of the molecule.

It is obvious that the groups designated $E^1$, $E^2$, $E^3$, $E^4$, R, W, X, Y and Z are to be selected so that the resulting compound of formula I is pharmaceutically acceptable.

In the known biphasic insulin preparations, it is common to combine fast acting, soluble insulin with prolonged acting, crystalline insulin in the same injection. Using compounds of formula I of this invention, a similar combined short and prolonged action can be obtained with a solution of a single compound of formula I. The ratio between short and long acting effect decreases as the concentration of zinc ions in the solution is increased.

Compounds of formula I may be prepared by a transpeptidation reaction in which a biosynthetic precursor compound having the correct insulin disulfide bridges and having the general formula II:

$$X—B(26-22)—E^4—B(20-14)—E^3—B(12-1) \atop | \atop B(28-29)—(Q_q—T)_r—A(1-3)—E^1—A(5-16)—E^2—A(18-20)—W \quad (II)$$

wherein Q is a peptide chain with q amino acids, q is an integer from 0 to 33, T is Lys or Arg, r is zero or one, and A, B, $E^1$, $E^2$, $E^3$, $E^4$, W and X each are as defined above, is reacted with an amino compound of the general formula III:

$$H—Y_m—Z_n—R_p \quad (III)$$

wherein Y, Z, R, m, n and p each are as defined above, and wherein side chain amino groups and hydroxy groups in Y and Z optionally are blocked with amino and hydroxy protecting groups, using trypsin or a trypsin like enzyme as a catalyst in a mixture of water and organic solvents analogously as described in U.S. Pat. No. 4,343,898. When W is hSer, nucleotides coding for Met are introduced at the A21 site in the gene. In the protein expressed conversion of Met into hSer is accomplished by cyanogen bromide. Preferred compounds of formula III for use in this process are Thr—NH$_2$, Lys(-Boc)—NH$_2$, Thr(Bu$^t$)—OBu$^t$, Thr—OBu$^t$, Ala—NH$_2$ and Arg(Boc)—NH$_2$. Amino groups may be derivatized by acylation with a fatty acid. Hydroxy groups may be protected by alkylation. If Y and Z contain groups which are reversibly blocked by amino protecting groups, these groups may be removed at a later stage, after the amino protected intermediate has been separated from the trypsin or trypsin like enzyme. Of the trypsin like enzymes, lysyl endopeptidase from *Achromobacter lyticus* is useful.

The compound of formula II may be expressed in a host organism such as yeast similar to the description in European patent application publication No. 163,529 of which the U.S. counterpart is S.N. 739,123, filed May 29, 1985 now U.S. Pat. No. 4,916,212, issued Apr. 10, 1990 using a gene having the correct codons for the amino acids in question. The gene encoding the novel insulin derivative is then inserted into a suitable expression vector which when transferred to yeast is capable of expressing the desired compound. The product expressed is then isolated from the cells or the culture broth depending on whether it is secreted from the cells or not.

An example of a reversible amino protecting group is tertiary butoxycarbonyl and a reversible hydroxy protecting group is tertiary butyl. Such groups are removed under conditions which do not cause undesired alteration in the compound of formula I, for example, by trifluoroacetic acid.

Changes in the A4, A17, A21, B13, B21 or B27 position may conveniently be introduced by genetic engineering, leaving for trypsin catalyzed semisynthesis to introduce the desired C-terminal residue of the B-chain.

The advantage in introducing the additional positive charges within the frame of the 51 amino acids of the insulin molecule to form the novel compounds of formula I rather than by prolongation of the B-chain beyond the 30 residues of the mammalian insulins relates to ease in preparation. In the semisynthetic transpeptidation, a large molar excess of the amino acid amide or amino acid ester is employed. If a dipeptide amide or ester were to be used in the transpeptidation reaction, either price or solubility or both are prohibitive for use in large.excess, and consequently the yield of the product becomes lower. Even when the same equimolar excess of, for example, Lys(Boc)—NH$_2$ or Lys(Boc)—Lys(Boc)—NH$_2$ is used in the transpeptidation reaction under similar conditions, the yield with the amino acid amide becomes substantially higher than with the dipeptide amide.

Insulin preparations of this invention are prepared by dissolving a compound of formula I in an aqueous medium at slightly acidic conditions, for example, in a concentration of 240 or 600 nmole/ml. The aqueous medium is made isotonic, for example, with sodium chloride, sodium acetate or glycerol. Furthermore, the aqueous medium may contain zinc ions in a concentrations of up to about 30 µg of Zn++ per nmol of compound of formula I, buffers such as acetate, citrate and histidine and preservatives such as m-cresol, nipagin or phenol. The pH value of the final insulin preparation depends upon the number of charges that have been changed in the compound of formula I, the concentration of zinc ions, the concentration of the compound of formula I and the compound of formula I selected. The pH value is adjusted to a value convenient for administration such as about 2.5–4.5, preventing precipitation. The insulin preparation is made sterile by sterile filtration.

The insulin preparations of this invention are used similarly to the use of the known insulin preparations.

Any novel feature or combination of features described herein is considered essential to this invention.

Herein the abbreviations used for the amino acids are those stated in J.Biol.Chem. 243 (1968), 3558. The amino acids stated herein are in L configuration. In formula I and elsewhere herein, A(1–3) is Gly-Ile-Val, A(5–6) is Gln-Cys etc., cf. the amino acid sequence of human insulin. Unless otherwise indicated, the species of insulins stated herein is human.

Synthesis of the insulin compounds

The source of insulin was an insulin precursor expressed in yeast as described in European patent application publication No. 163.529 of which the U.S. counterpart is S.N. 739,123, filed May 29, 1985 now U.S. Pat. No. 4,916,212. issued Apr. 10, 1990.

The insulin precursors were recovered from the fermentation broths by adsorption to LICHROPREP TM RP-18 as described in Example 7 of the same European patent application. The precursors were eluted from the column with 0.2 M KCl, 0.001 M HCl in 33% (v/v) ethanol. The insulin precursors were crystallized from the pool by successive additions of water (1 volume per volume of pool), solid trisodium citrate to obtain a molarity of 0.05 M and finally zinc acetate to obtain a molarity of 0.006 M. The pH value was adjusted to 6.8 and the mixture was left overnight at 4° C. The crystals were isolated by centrifugaton, washed with water and dried in vacuo.

Protected amino acids and protected peptides for enzymatic semisynthesis were either prepared by standard methods or purchased (custom synthesis) from either Nova Biochem or Bachem, both Switzerland.

The letters TM after a name indicates that it is a trade mark.

In the starting material in Examples 1 through 14, $(Q_q-T)_r$ of formula II was chosen to Ala-Ala-Lys and constructed as described for yeast plasmid pMT610 in Example 10 in European patent application publication No. 163.529. Nucleotides coding for Gln$^{B13}$, Gln$^{A17}$, Arg$^{B27}$, Lys$^{B27}$, Asp$^{A21}$, Gly$^{A21}$, His$^{A21}$, Ser$^{A21}$ and Thr$^{A21}$ were substituted in pMT610 by site specific mutagenesis using the procedure in Nucl.Acids.Res. 11 (1983), 5103–5112.

EXAMPLE 1

Synthesis of His$^{A21}$, Arg$^{B27}$ human insulin

The title compound was synthesized from the corresponding single chain insulin precursor, viz. His$^{A21}$,Arg$^{B27}$, B(1–29)-Ala-Ala-Lys-A(1–21), using methods analog to those described in Example A. Yields, charges relative to human insulin, rates of migration relative to insulin in DISC PAGE electrophoresis at pH 8.9 and deviations in amino acid compositions from human insulin appear from Table I, below.

EXAMPLES 2–8

Synthesis of Asp$^{A21}$,Arg$^{B27}$, Thr$^{B30}$—NH$_2$ human insulin,
Gly$^{A21}$,Arg$^{B27}$,Thr$^{B30}$—NH$_2$ human insulin,
His$^{A21}$,Arg$^{B27}$,Thr$^{B30}$—NH$_2$ human insulin,
Gly$^{A21}$,Arg$^{B27}$,Gln$^{B13}$Thr —NH$_2$ 2 human insulin,
Ser$^{A21}$,Arg$^{B27}$,Gln$^{B13}$Thr$^{B30}$—NH$_2$ human insulin,
Thr$^{A21}$,Arg$^{B27}$,Gln$^{B13}$Thr$^{B30}$—NH$_2$ human insulin and
Ser$^{A21}$,Arg$^{B27}$,Thr$^{B30}$—NH$_2$ human insulin
Asp$^{A21}$,Arg$^{B27}$,B(1-29) —Ala—Ala—Lys—A(1-21),
Gly$^{A21}$,Arg$^{B27}$,B(1-29) —Ala—Ala—Lys—A(1-21),
His$^{A21}$,Arg$^{B27}$,B(1-29) —Ala—Ala—Lys—A(1-21),
Gly$^{A21}$,Arg$^{B27}$,B(1-29) —Ala—Ala—Lys—A(1-21),
Ser$^{A21}$,Arg$^{B27}$,B(1-29) —Ala—Ala—Lys—A(1-21),
Thr$^{A21}$,Arg$^{B27}$,B(1-29) —Ala—Ala—Lys—A(1-21) and Ser$^{A21}$,Arg$^{B27}$,B(1-29)—Ala—Ala—Lys—A(1-21) transpeptidation in organic aqueous solution in the presence of Thr—HN$_2$ as described in European patent application publication No. 194.864, Examples 4 and 6. Yields, charges relative to human insulin, rates of migration relative to insulin in DISC PAGE electrophoresis at pH 8.9 and deviations in amino acid compositions from human insulin appear from Table I.

EXAMPLE 9

Synthesis of Asp$^{A21}$,Arg$^{B27}$,Lys$^{B30}$—NH$_2$ human insulin

The title compound was synthesized from the corresponding single chain insulin precursor, viz. Asp$^{A21}$,Arg$^{B27}$, B(1-29)—Ala—ala—Lys—A(1-21) by tryptic transpeptidation in organic aqueous solution int he presence of Lys(Boc)—NH$_2$, purification of the intermediate, Lys(Boc)$^{B30}$—NH$_2$ human insulin, followed by removal of the Boc protecting grou by TFA as described in European patent application publication No. 194.864, Examples 5 and 7. Yield and analytical data are shown in Table I.

TABLE I

| Substitution in human insulin | Yield, % | Charge relative to human insulin at pH 7 | Rate of migration at pH 8.9, % relative to human insulin | Deviations in amino acid compositions from human insulin after acid hydrolysis, residues/molecule |
|---|---|---|---|---|
| His$^{A21}$, Arg$^{B27}$ | 16 | +1.1 | 75 | +1 His, +1 Arg, −1 Asp, −1 Thr |
| Asp$^{A21}$, Arg$^{B27}$, Thr$^{B30}$—NH$_2$ | 23 | +1 | 75 | +1 Arg, −1 Thr |
| Gly$^{A21}$, Arg$^{B27}$, Thr$^{B30}$—NH$_2$ | 32 | +2 | 55 | +1 Gly, +1 Arg, −1 Asp, −1 Thr |
| His$^{A21}$, Arg$^{B27}$, Thr$^{B30}$—NH$_2$ | 20 | +2.1 | 55 | +1 His, +1 Arg, −1 Asp, −1 Thr |
| Gly$^{A21}$, Arg$^{B27}$, Gln$^{B13}$, Thr$^{B30}$—NH$_2$ | 23 | +3 | 35 | +1 Gly, +1 Arg, −1 Asp, −1 Thr |
| Ser$^{A21}$, Arg$^{B27}$, Gln$^{B13}$, Thr$^{B30}$—NH$_2$ | 21 | +3 | 35 | +1 Ser, +1 Arg, −1 Asp, −1 Thr |
| Thr$^{A21}$, Arg$^{B27}$, Gln$^{B13}$, Thr$^{B30}$—NH$_2$ | 29 | +3 | 35 | +1 Arg, −1 Asp |
| Ser$^{A21}$, Arg$^{B27}$, Thr$^{B30}$—NH$_2$ |  | +2 | 55 | +1 Ser, +1 Arg, −1 Asp, −1 Thr |
| Asp$^{A21}$, Arg$^{B27}$, Lys$^{B30}$—NH$_2$ | 13 | +2 | 55 | +1 Arg, +1 Lys, −2 Thr |

EXAMPLE 10

Preparation of injectable solutions of compounds of formula I

Sterile injectable solutions of the compounds of formula I for testing of the degree of prolonged action were made using 1.6% (w/v) glycerol as the isotonicum, using 0.3% (w/v) m-cresol as the preservative, and being buffered with 0.01 M sodium acetate. The concentration of zinc ions was 8 or 80 µg/ml. the pH values of the solutions were adjusted sufficiently off the isoelectric point of the compounds of formula I to keep the solutions clear upon storage at 4°C. The solutions contained 240 nmole/ml of the compounds of formula I. The concentration of 240 nmole/ml was established by measurement of the absorbance at 276 nm of a more concentrated stock solution devoid of m-cresol, using the molar extinction coefficient for porcine insulin of 6100 for these derivatives (see Handbuch der Inneren Mdiizin, vol. 7/Part 2A, Editor: oberdisse, 1975, 113). For monocomponent procine insulin, the established potency is 28.5 U/mg dry substance (see Diabetes Care, Vol. 6/Supplement 1 (1983), 4), viz. 1 U corresponds to 5.95 nmole.

Injectable solutions containing 240 nmole/ml of the compounds of formula I stated in Table II and having the pH values and content of zinc stated therein were made.

Test for prolongation of insulin effect

The prolongation of the hypoglycemic effect produced by the injectable solutions of insuline was tested according to British Pharmacopoeia 1980, a 142, in fasted rabbits. Each test solution was administered subcutaneously in a dosis of 14.3 nmole per rabbit in 12 animals weighing 3-4 kg, and the course of the hypoglycemia was followed for 6 hours. For comparison the fast acting preparation ACTRAPID TM porcine insulin and the intermediate acting MONOTARD TM human insulin, were included in the tests. The results of the tests are shown in Table II.

TABLE II

| Compound of formula I | Zn$^{++}$, µg/ml | pH | Glucose in percent of initial | | | |
|---|---|---|---|---|---|---|
| | | | 1 h | 2 h | 4 h | 6 h |
| Asp$^{A21}$, Arg$^{B27}$, Thr$^{B30}$—NH$_2$ human insulin | 80 | 4 | 60 | 54 | 58 | 60 |
| Asp$^{A21}$, Arg$^{B27}$, Lys$^{B30}$—NH$_2$ human insulin | 80 | 4 | 72 | 67 | 61 | 59 |
| Gly$^{A21}$, Arg$^{B27}$, Thr$^{B30}$—NH$_2$ human insulin | 8 | 4 | 59 | 62 | 71 | 74 |
| Gly$^{A21}$, Arg$^{B27}$, Thr$^{B30}$—NH$_2$ human insulin | 80 | 4 | 72 | 73 | 74 | 74 |
| His$^{A21}$, Arg$^{B27}$ human insulin | 80 | 4 | 65 | 53 | 66 | 88 |
| His$^{A21}$, Arg$^{B27}$, Thr$^{B30}$—NH$_2$ human insulin | 80 | 4 | 61 | 52 | 52 | 72 |
| Gly$^{A21}$, Arg$^{B27}$, Gln$^{B13}$, Thr$^{B30}$—NH$_2$ human insulin | 80 | 4 | 82 | 86 | 85 | 90 |
| Ser$^{A21}$, Arg$^{B27}$, Gln$^{B13}$, Thr$^{B30}$—NH$_2$ human insulin | 80 | 4 | 90 | 91 | 88 | 92 |
| Thr$^{A21}$, Arg$^{B27}$, Gln$^{B13}$, Thr$^{B30}$—NH$_2$ human insulin | 80 | 4 | 90 | 90 | 88 | 93 |
| Ser$^{A21}$, Arg$^{B27}$, Thr$^{B30}$—NH$_2$ human insulin | 80 | 4 | 60 | 62 | 64 | 68 |
| ACTRAPID TM porcine insulin | 15 | 7 | 46 | 44 | 74 | 91 |
| MONOTARD TM human insulin | 80 | 7 | 54 | 43 | 50 | 74 |

The potencies of insulin compounds were assessed in the mouse blood sugar depletion test (British Pharmacopoeia 1980, A 141-A 142). In order to minimize the problem of estimating potency of insulins having a timing different from the standard, insulin solutions for potency determinations were made up without additions of zinc. Solutions were made up to contain 240 nmole/ml based on the absorbance at 276 nm. The zinc content of solutions were 8-10 µg/ml, arizing from the crystalline derivatives. The estimated potencies of some insulin compounds are shown in Table III, below.

TABLE III

| | Potency relative to insulin, % | Confidence limits (P = 0.05), % |
|---|---|---|
| Asp$^{A21}$, Arg$^{B27}$, Thr$^{B30}$—NH$_2$ | 83 | 92-74 |

TABLE III-continued

| | Potency relative to insulin, % | Confidence limits (P = 0.05), % |
|---|---|---|
| human insulin Asp$^{A21}$, Arg$^{B27}$, Lys$^{B30}$—NH$_2$ human insulin | 69 | 77–62 |
| Gly$^{A21}$, Arg$^{B27}$, Thr$^{B30}$—NH$_2$ human insulin | 75 | 83–68 |
| His$^{A21}$, Arg$^{B27}$ human insulin | 71 | 79–63 |
| His$^{A21}$, Arg$^{B27}$, Thr$^{B30}$—NH$_2$ human insulin | 72 | 81–64 |
| Gly$^{A21}$, Arg$^{B27}$, Gln$^{B13}$, Thr$^{B30}$—NH$_2$ human insulin | 49 | 54–44 |
| Ser$^{A21}$, Arg$^{B27}$, Gln$^{B13}$, Thr$^{B30}$—NH$_2$ human insulin | 47 | 54–40 |
| Thr$^{A21}$, Arg$^{B27}$, Gln$^{B13}$, Thr$^{B30}$—NH$_2$ human insulin | 28 | 32–24 |
| Ser$^{A21}$, Arg$^{B27}$, Thr$^{B30}$—NH$_2$ human insulin | 76 | 83–68 |

EXAMPLE 11

Di- and polymerization products formed per month after storage at 25 C.

The compositions tested were as follows: 0.24 mM insulin analog, 0.3% /w/v) m-cresol, 1.6% (w/v) glycerol, 0.01 M sodium acetate and 3 Zn$^{++}$ per insulin hexamer. The determination was made using HPSEC (high performance size exclusion chromatography).

The results obtained appears from Table IV. A reference insulin having Asn$^{A21}$ is included for comparison.

TABLE IV

| | pH of formulation | | |
|---|---|---|---|
| Insulin analog | 3.0 | 4.0 | 5.0 |
| Arg$^{B27}$Thr$^{B30}$—NH$_2$ human insulin | 0.15% | 0.62% | 1.4% |
| Gly$^{A21}$, Arg$^{B27}$, Thr$^{B30}$—NH$_2$ human insulin | 0.01–0.03% | 0.02–0.05% | 0.20% |
| His$^{A21}$, Arg$^{B27}$ human insulin | 0.01–0.04% | | |
| Asp$^{A21}$, Arg$^{B27}$, Thr$^{B30}$—NH$_2$ human insulin | 0.03% | 0.15% | 0.14% |

EXAMPLE 12

Deamidation products formed per month after storage 25 at 25° C. and a pH value of 3.

The compositions tested were as follows: 0.24 mM insulin analog, 0.3% (w/v) m-cresol, 1.6% (w/v) glycerol, 3 Zn$^{++}$ per insulin hexamer and 0.01 M sodium acetate to obtain a pH value of 3. The determinations were made using DISC PAGE analysis.

The results obtained appears from Table V. A reference insulin having Asn$^{A21}$ is included for comparison.

TABLE V

| Arg$^{B27}$Thr$^{B30}$—NH$_2$ human insulin | approx. 10% |
|---|---|
| Gly$^{A21}$, Arg$^{B27}$, Thr$^{B30}$—NH$_2$ human insulin | below 0.5% |
| His$^{A21}$, Arg$^{B27}$ human insulin | below 0.5% |
| Asp$^{A21}$, Arg$^{B27}$, Thr$^{B30}$—NH$_2$ human insulin | below 0.5% |

EXAMPLE A

Synthesis of Gln$^{13}$, Arg$^{B27}$ human insulin

To a suspension of 5 g of Gln$^{B13}$Arg$^{B27}$, B(1-29)-Ala-Ala-Lys-A(1-21) insulin precursor in 50 ml of 2 M Thr-OBu$^t$,CH$_3$ COOH (L-threonine tert.butyl ester, hydroacetate salt) in DMF, 25 ml of 25.5% (v/v) water in DMF (25.5 ml water, DMF to make 100 ml) was added. The suspension was cooled to 12° C. under stirring. A solution of 0.5 g of porcine trypsin in 12.5 ml of a 0.05 M aqueous solution of calcium acetate was added. Stirring was continued until dissolution. After 48 hours at 12° C., the proteins were precipitated by pouring the mixture into 600 ml of acetone. The precipitate was isolated by centrifugaton, washed once with 200 ml of acetone, isolated by centrifugation and dried in a stream of nitrogen. The precipitate was dissolved in 100 ml of 0.04 N hydrochloric acid, the pH value was adjusted to 2.5 and the solution was applied to a 5×30 cm preparative high pressure liquid chromatography (hereinafter designated HPLC) column packed with silica particles substituted with octadecyldimethylsilyl (mean particle size 15 micron, pore size 100 Angstrom). The column was equilibrated with ethanol/0.3 M aqueous solution of potassium chloride, 0.001 N hydrochloric acid, in a ratio of 35.5/64.5 (parts per volume). The proteins were eluted from the column with the same buffer at a rate of 2 liter/h. Gln$^{B13}$Arg$^{B27}$, Thr$^{B30}$—OBu$^t$ human insulin was found in a peak emerging from the column between 55 and 100 min. The Gln$^{B13}$Arg$^{B27}$, Thr$^{B30}$-OBu$^t$ human insulin was isolated from the pool by successive additions of water to make ethanol concentration 15% (v/v), solid trisodium citrate to obtain a molarity of 0.05 M with respect to citrate and solid zinc chloride to obtain a molarity of 0.006 M with respect to zinc. The pH value was adjusted to 6.8 and after 1 hour at room temperature, the crystallisation was continued at 4° C. for 24 hours with stirring. The crystals were spun down, washed twice with 20 ml of ice-cold water, spun down and dried in vacuo. Yield: 2.51 g of Gln$^{B13}$Arg$^{B27}$, Thr$^{B30}$-OBu$^t$ human insulin.

Gln$^{B13}$Arg$^{B27}$, Thr$^{B30}$—OBu$^t$ human insulin was dissolved in 100 ml of trifluoroacetic acid and left for 2 hours at room temperature. The trifluoroacetic acid was removed by lyophilization. The lyophilisate was dissolved in 100 ml of water, the pH value adjusted to 2.5 and 20 g of sodium chloride was added. The salt cake consisting of Gln$^{B13}$Arg$^{B27}$ human insulin was isolated by centrifugation. The salt cake was dissolved in 850 ml of water and Gln$^{B13}$Arg$^{B27}$ human insulin was crystallized by successive additions of 150 ml of ethanol, 14.7 g of trisodium citrate, dihydrate and 0.82 g of zinc chloride followed by adjustment of the pH value to 6.8. After 1 hour at room temperature, the crystallisation was continued at 4° C. for 24 hours with gentle stirring. The crystals were spun down, washed twice with 20 ml of ice-cold water, spun down and dried in vacuo. yield: 1.71 g of Gln$^{B13}$Arg$^{B27}$ human insulin, corresponding to 36%.

The amino acid composition was in agreement with the theory, arginine and threonine both being 2 residues/molecule. The product was pure in DISC PAGE electrophoresis, the rate of migration being 55% of that of human insulin corresponding to a difference in charges of about 2. For details of the DISC PAGE electrophoresis see Horm.Metab.Res. Supplement Series No. 5 (1974), 134. The content of zinc in the crystals was 0.42% (weight/weight).

For completeness it is noted that novel insulin analogs of non-human sequence fall within practice of this invention. Both a proper but not necessarily the human peptide sequence and an insulin activity are contemplated herein as within the term insulin. As has already been indicated all amino acid residues in the peptide sequence that is human insulin are not required for insulin activity. A notable instance in the nominal difference between porcine insulin and human insulin, B30 being Ala in porcine insulin. Ser is at B30 in rabbit insulin. Both these animal insulins contain Asn at A21. A different residue than Asn at A21 may be substituted advantageously in these non-human insulins. Although human insulin analogs are preferred modes of this invention, many years of use and experience with porcine insulin demonstrate their utility and accordingly that a substitution for Asn at A21, e.g., by Gly, Ser, Thr, Ala or hSer, is advantageous in such insulins.

1. Preparation of a gene coding for human proinsulin B-C-A

Total RNA purified (Chirgwin, J. M. Przybyla, A. E., McDonald, R. J. & Rutter, W. J., Biochemistry 18, (1979) 5294-5299) from human pancreas was reverse transcribed (Boel, E., Vuust, J., Norris, F., Norris, K., Wind, A., Rehfeld, J. F. & Marcker, K. A., Proc.Nacl..Acad.Sci. U.S.A. 80, (1983), 2866-2869) with AMV reverse transcriptase and d(GCTTTATT-CCATCTCTC) as 1. strand primer. After preparative urea-polyacrylamide gel purification of the human proinsulin cDNA, the second strand was synthesized on this template with DNA polymerase large fragment and d(CAGATCACTGTCC) and 2nd strand primer. After S1 nuclease digestion the human proinsulin ds. cDNA was purified by polyacrylamide gel electrophoresis, tailed with terminal transferase and cloned in the PstI site on pBR327 (Sorberon et al., Gene 9, (1980), 297-305) in E. coli. A correct clone harbouring a plasmid containing a gene encoding human proinsulin B-C-A was identified from the recombinants by restriction endonuclease analysis and confirmed by nucleotide sequencing (Maxam, A., and Gilbert, W., Methods in Enzymology, 65 (1980), 499-560. Sanger, F., Nicklen, S. & Coulson, A. R., Proc.Natl.Acad.Sci. U.S.A. 74, (1977), 5463-5467).

2. Preparation of genes coding for precursors of human insulin

The gene encoding B(1-29)-A(1-21) of human insulin was made by side specific mutagenesis of the human proinsulin sequence with a 75 bp in frame deletion in the C-peptide coding region inserted into a circular single stranded M-13 bacteriophage vector. A modified procedure (K. Norris et al., Nucl.Acids.Res. 11 (1983) 5103-5112) was used in which a chemically synthesized 19-mer deletion primer was annealed to the M13 template. After a short enzymatic extension reaction a "universal" 15-mer M13 dideoxy sequencing primer was added followed by enzymatic extension and ligation. A double stranded restriction fragment (BamHI-Hind III) was cut out of the partly double stranded circular DNA and ligated into pBR322 cut with BamHI and Hind III.

The obtained ligation mixture was used to transform E. coli and transformants harbouring a plasmid pMT319 containing the gene encoding B(1-29)-A(1-21) of human insulin were identified.

Genes encoding B(1-29)-Ala-Ala-Lys-A(1-21) and B(1-29)-Ser-Lys-A(1-21) were made accordingly by insertion of a fragment encoding MFα1-B-C-A in the M-13 bacteriophage and site specific mutagenesis of the human proinsulin sequence with chemically synthesized 30-mer and 27-mer deletion primers, respectively, and the above mentioned "universal" 15-mer M13 dideoxy sequencing primer. A double stranded restriction fragment (XbaI-EcoRl) was cut out of the partly double stranded circular DNA and ligated into pUC13 and pT5, respectively. By transformation and retransformation of E. coli, transformants harbouring a plasmia pMT598 containing the gene encoding B(1-29)-Ala-Ala-Lys-A(1-21) and pMT630 containing the gene encoding B(1-29)-Ser-Lys-A(1-21) were identified.

A gene encoding B(1-29)-Thr-Arg-Glu-Ala-Glu-Asp-Leu-Gln-Lys-A(1-21) was made in a similar way as described above by insertion of a fragment encoding MFα1-B(1-29)-A(1-21) in a M13 mp11 bacteriophage and site specific mutagenesis of the B(1-29)-A(1-21) sequence with a chemically synthesized 46-mer deletion primer (5'-CACACCCAAGACTAAAGAAGCT-GAAGACTTGCAAAGAGGCATTGTG-3') and the "universal" primer. Also, by a similar procedure a gene encoding B(1-29)-Thr-Arg-Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln-Lys-A(1-21) was constructed.

3. Plasmid constructions

The gene encoding B(1-29)-A(1-21) of human insulin (B'A) was isolated as a restriction fragment from pMT319 and combined with fragments coding for the TPI promoter (TPI$_p$) (T. Alber and G. Kawasaki. Nucleotide Sequence of the Triose Phosphate Isomerase Gene of Saccharomyces cerevisiae. J.Mol. Applied Genet. 1 (1982) 419-434), the MFα1 leader sequence (J. Kurjan and I. Herskowitz., Structure of a Yeast Pheromone Gene (MFα): A Putative α-Factor Precursor Contains four Tandem Copies of Mature α-Factor. Cell 30 (1982) 933-943) and the transcription termination sequence from TPI of S.cerevisiae (TPI$_T$). These fragments provide sequences to ensure a high rate of transcription for the B'A encoding gene and also provide a presequence which can effect the localization of B'A into the secretory pathway and its eventual excretion into the growth medium. This expression unit for B'A (TPI$_P$-MFα1 leader - B'A - TPI$_T$ was then placed on a plasmid vector containing the yeast 2μ origin of replication and a selectable marker, LEU 2, to give pMT344, a yeast expression vector for B'A.

During in vivo maturation of α-factor in yeast, the last (C-terminal) six amino acids of the MFα1 leader peptide (Lys-Arg-Glu-Ala-Glu-Ala) are removed from the α-factor precursor by the sequential and an aminodipeptidase which removes the Glu-Ala residues (Julius, D. et al. Cell 32 (1983) 839-852). To eliminate the need for the yeast aminodipeptidase, the sequence coding for the C-terminal Glu-Ala-Glu-Ala of the MFα1 leader was removed via in vitro mutagenesis. The resulting yeast expression plasmid, pMT475, contains the insert coding for TPI$_P$-MFα1 leader (minus Glu-Ala-Glu-Ala) - B'A - TPI$_T$.

In a preferred construction the modified expression unit was transferred to a stable, high copy number yeast plasmid CPOT, (ATCC No. 39685), which can be selected merely by the presence of glucose in the growth medium. The resulting yeast expression vector for B'A was numbered pMT479.

The fragment encoding MFα1 leader (minus Glu-Ala-Glu-Ala)-B(1-29)-Ala-Ala-Lys-A(1-21) was isolated as a restriction fragment from pMT598 and combined with fragments coding for the TPI promoter and the TPI terminator and transferred to the above mentioned high copy number yeast plasmid CPOT. The resulting yeast expression vector for B(1-29)-Ala-Ala-Lys-A(1-21) was numbered pMT610.

The fragment containing the insert TPI$_P$- MFα1 leader (minus Glu-Ala-Glu-Ala)-B(1-29)-Ser-Lys-A(1-21)-TPI$_T$ was isolated as a restriction fragment from pMT630 and transferred into CPOT. The resulting yeast expression vector for B(1-29)-Ser-Lys-A(1-21) was numbered pMT639.

The fragment containing the insert TPI$_P$- MFα1 leader-(minus Glu-Ala-Glu-Ala)B(1-29)-Thr-Arg-Glu-Ala-Glu-Asp-Leu-Gln-Lys-A(1-21)-TPI$_T$ was inserted into a high copy number yeast plasmid DPOT, being a CPOT derivative containing a SphI-BamHI-fragment of pBR322 inserted into a SpHl-BamHI fragment of CPOT. The resulting yeast expression vector for B(1-29)-Thr-Arg-Glu-Ala-Glu-Asp-Leu-Gln-Lys-A(1-21) was numbered p1126.

4. Transformation

Plasmids pMT344 and pMT475 were transformed into *S. cerevisiae* leu 2 mutants by selection for leucin prototrophy as described by Hinnen et al. (A. Hinne, J. B. Hicks and G. R. Fink. Transformation of Yeast. Proc.Nat.Aca.Sci 75 (1978) 1929).

Plasmids pMT479, pMT610, pMT639 and p1126 were transformed into *S. cerevisiae* strains carrying deletions in the TPI gene by selecting for growth on glucose. Such strains are normally unable to grow on glucose as the sole cardon source and grow very slowly on galactose lactate medium. This defect is due to a mutation in the triose phosphate isomerase gene, obtained by deletion and replacement of a major part of this gene with the *S. cerevisiae* LEU 2 gene. Because of the growth deficiencies there is a strong selection for a plasmid which contains a gene coding for TPI. pMT479 contains the Schizo. pombe TPI gene.

5. Expression of human insulin precursors in yeast

Expression products of human insulin type were measured by radioimmunoassay for insulin as described by Heding, L. (Diabetologia 8, 260-66, 1972) with the only exception that the insulin precursor standard in question was used instead of an insulin standard. The purity of the standards were about 98% as determined by HPLC and the actual concentration of peptide in the standard was determined by amino acid analysis. The expression levels of immunoreactive human insulin precursors in the transformed yeast strains are summarized in Table 1.

TABLE 1

| Yeast strain | Plasmid | Construct | Immunoreactive insulin precursor (nmol/l supernatant) |
|---|---|---|---|
| Expression levels of immunoreactive human insulin precursors in yeast. | | | |
| MT 350 (DSM 2957) | pMT 344 | B(1-29)-A(1-21) | 100 |
| MT 371 (DSM 2958) | pMT 475 | B(1-29)-A(1-21) | 192 |
| MT 519 (DSM 2959) | pMT 479 | B(1-29)-A(1-21) | 2900 |
| MT 620 (DSM 3196) | pMT 610 | B(1-29)-Ala—Ala—Lys—A(1-21) | 1200-1600 |
| MT 649 (DSM 3197) | pMT 639 | B(1-29)-Ser—Lys—A(1-21) | 1600 |
| ZA 426 | p1126 | B(1-29)-Thr—Arg—Glu—Ala—Glu—Asp—Leu—Gln—Lys—A(1-21) | 200 |

6. Conversion of human insulin precursor into B30 esters of human insulin

The conversion of the human insulin precursors into human insulin esters can be followed quantitatively by HPLC (high pressure liquid chromatography) on reverse phase. A 4×300 mm "μBondapak C18 column" (Waters Ass.) was used and the elution was performed with a buffer comprising 0.2 M ammonium sulphate (adjusted to a pH value of 3.5 with sulphuric acid) and containing 26-50% acetonitrile. The optimal acetonitrile concentration depends on which ester on desires to separate from the insulin precursor. In case of human insulin methyl ester separation is achieved in about 26% (v/v) of acetonitrile.

Before the application on the HPLC column the proteins in the reaction mixture was precipitated by addition of 10 volumes of acetone. The precipitate was isolated by centrifugation, dried in vacuo, and dissolved in 1 M acetic acid. The depository DSM is Deutsche Sammlung von Mikroorganismen, Grisebochstrasse 8, D-3400 Göttingon, West Germany.

We claim:

1. A human insulin analog having an amino acid residue at A21, selected from the group consisting of Glu, Asp, Lys, Arg, His, Val, Gln, Ile, Phe, Tyr, Met, Gly, Ser, Thr, Ala, Leu, Trp and hSer, and, wherein at least one of the amino acid residues at A4, A17, B13, and B21 is a neutral amino acid residue selected from the group consisting of Gly, Val, Ile, Leu, Phe, Tyr, Met, Asn, Gln, Ala, Ser and Thr with the proviso that the insulin analog has at least one charge more than human insulin at a pH value of 7.

2. A human insulin analog having an amino acid residue at A21, selected from the group consisting of Glu, Asp, Lys, Arg, His, Val, Gln, Ile, Phe, Tyr, Met, Gly, Ser, Thr, Ala, Leu, Trp and hSer, and wherein the B27 amino acid residue is Lys or Arg with the provisio that the insulin analog has at least one charge more than human insulin at a pH value of 7.

3. An aqueous solution of a human insulin analog having an amino acid residue at A21, selected from the group consisting of Glu, Asp, Lys, Arg, His, Val, Gln, Ile, Phe, Tyr, Met, Gly, Ser, Thr, Ala, Leu, Trp and hSer, wherein at least one of the amino acid residues at A4, A17, B13, and B21 is a neutral amino acid residue selected from the group consisting of Gly, Val, Ile, Leu, Phe, Tyr, Met, Asn, Gln, Ala, Ser and Thr, wherein the B27 amino acid residue is Lys or Arg, and wherein the C-terminal carboxyl group of the B-chain is amidated at a pH value of 2.5-5.8 with the proviso that the insulin analog has at least one charge more than human insulin at a pH value of 7.

4. A human insulin analog selected from the group consisting of:

Gly$^{A21}$,Lys$^{B27}$,Thr$^{B30}$—NH$_2$ human insulin,
Ser$^{A21}$,Lys$^{B27}$,Thr$^{B30}$—NH$_2$ human insulin,
Thr$^{A21}$,Lys$^{B27}$,Thr$^{B30}$—NH$_2$ human insulin,
Ala$^{A21}$,Lys$^{B27}$,Thr$^{B30}$—NH$_2$ human insulin,
His$^{A21}$,Lys$^{B27}$,Thr$^{B30}$—NH$_2$ human insulin, Asp$^{A21}$,Lys$^{B27}$,Thr$^{B30}$—NH$_2$ human insulin,
Gly$^{A21}$,Arg$^{B27}$,Thr$^{B30}$—NH$_2$ human insulin,
Ser$^{A21}$,Arg$^{B27}$,Thr$^{B30}$—NH$_2$ human insulin,
Thr$^{A21}$,Arg$^{B27}$,Thr$^{B30}$—NH$_2$ human insulin,
Ala$^{A21}$,Arg$^{B27}$,Thr$^{B30}$—NH$_2$ human insulin,
His$^{A21}$,Arg$^{B27}$,Thr$^{B30}$—NH$_2$ human insulin,
Asp$^{A21}$,Arg$^{B27}$,Thr$^{B30}$—NH$_2$ human insulin,
Gln$^{B13}$,Gly$^{A21}$,Arg$^{B27}$, Thr$^{B30}$—NH$_2$ human insulin,
Gln$^{B13}$,Ser$^{A21}$,Arg$^{B27}$, Thr$^{B30}$—NH$_2$ human insulin,
Gln$^{B13}$,Thr$^{A21}$,Arg$^{B27}$, Thr$^{B30}$—NH$_2$ human insulin,
Gln$^{B13}$,Ala$^{A21}$,Arg$^{B27}$, Thr$^{B30}$—NH$_2$ human insulin,
Gln$^{B13}$,His$^{A21}$,Arg$^{B27}$, Thr$^{B30}$—NH$_2$ human insulin,
Gln$^{B13}$,Asp$^{A21}$,Arg$^{B27}$, Thr$^{B30}$—NH$_2$ human insulin,
Gln$^{B13}$,Gly$^{A21}$,Lys$^{B27}$, Thr$^{B30}$—NH$_2$ human insulin,
Gln$^{B13}$,Ser$^{A21}$,Lys$^{B27}$, Thr$^{B30}$—NH$_2$ human insulin,
Gln$^{B13}$,Thr$^{A21}$,Lys$^{B27}$, Thr$^{B30}$—NH$_2$ human insulin,
Gln$^{B13}$,Ala$^{A21}$,Lys$^{B27}$, Thr$^{B30}$—NH$_2$ human insulin,
Gln$^{B13}$,His$^{A21}$,Lys$^{B27}$, Thr$^{B30}$—NH$_2$ human insulin,
Gln$^{B13}$,Asp$^{A21}$,Lys$^{B27}$, Thr$^{B30}$—NH$_2$ human insulin,
Ser$^{A21}$,Lys$^{B27}$ human insulin,
Thr$^{A21}$,Lys$^{B27}$ human insulin,
Ala$^{A21}$,Lys$^{B27}$ human insulin,
His$^{A21}$,Lys$^{B27}$ human insulin,
Asp$^{A21}$,Lys$^{B27}$ human insulin,
Gly$^{A21}$,Lys$^{B27}$ human insulin and
Ser$^{A21}$,Arg$^{B27}$ human insulin.

5. An aqueous solution of a human insulin analog selected from the group consisting of:
Gly$^{A21}$,Lys$^{B27}$,Thr$^{B30}$—NH$_2$ human insulin,
Ser$^{A21}$,Lys$^{B27}$,Thr$^{B30}$—NH$_2$ human insulin,
Thr$^{A21}$,Lys$^{B27}$,Thr$^{B30}$—NH$_2$ human insulin,
Ala$^{A21}$,Lys$^{B27}$,Thr$^{B30}$—NH$_2$ human insulin,
His$^{A21}$,Lys$^{B27}$,Thr$^{B30}$—NH$_2$ human insulin,
Asp$^{A21}$,Lys$^{B27}$,Thr$^{B30}$—NH$_2$ human insulin,
Gly$^{A21}$,Arg$^{B27}$,Thr$^{B30}$—NH$_2$ human insulin,
Ser$^{A21}$,Arg$^{B27}$,Thr$^{B30}$—NH$_2$ human insulin,
Thr$^{A21}$,Arg$^{B27}$,Thr$^{B30}$—NH$_2$ human insulin,
Ala$^{A21}$,Arg$^{B27}$,Thr$^{B30}$—NH$_2$ human insulin,
His$^{A21}$,Arg$^{B27}$,Thr$^{B30}$—NH$_2$ human insulin,
Asp$^{A21}$,Arg$^{B27}$,Thr$^{B30}$—NH$_2$ human insulin,
Gln$^{B13}$,Gly$^{A21}$,Arg$^{B27}$, Thr$^{B30}$—NH$_2$ human insulin,
Gln$^{B13}$,Ser$^{A21}$, Arg$^{B27}$,Thr$^{B30}$—NH$_2$ human insulin,
Gln$^{B13}$,Thr$^{A21}$, Arg$^{B27}$,Thr$^{B30}$—NH$_2$ human insulin,
Gln$^{B13}$,Ala$^{A21}$, Arg$^{B27}$,Thr$^{B30}$—NH$_2$ human insulin,
Gln$^{B13}$,His$^{A21}$, Arg$^{B27}$,Thr$^{B30}$—NH$_2$ human insulin,
Gln$^{B13}$,Asp$^{A21}$, Arg$^{B27}$,Thr$^{B30}$—NH$_2$ human insulin,
Gln$^{B13}$,Gly$^{A21}$, Lys$^{B27}$,Thr$^{B30}$—NH$_2$ human insulin,
Gln$^{B13}$,Ser$^{A21}$, Lys$^{B27}$,Thr$^{B30}$—NH$_2$ human insulin,
Gln$^{B13}$,Thr$^{A21}$, Lys$^{B27}$,Thr$^{B30}$—NH$_2$ human insulin,
Gln$^{B13}$,Ala$^{A21}$, Lys$^{B27}$,Thr$^{B30}$—NH$_2$ human insulin,
Gln$^{B13}$,His$^{A21}$, Lys$^{B27}$,Thr$^{B30}$—NH$_2$ human insulin,
Gln$^{B13}$,Asp$^{A21}$, Lys$^{B27}$, Thr$^{B30}$—NH$_2$ human insulin,
Ser$^{A21}$,Lys$^{B27}$ human insulin,
Thr$^{A21}$,Lys$^{B27}$ human insulin,
Ala$^{A21}$,Lys$^{B27}$ human insulin,
His$^{A21}$,Lys$^{B27}$ human insulin,
Asp$^{A21}$,Lys$^{B27}$ human insulin,
Thr$^{A21}$,Arg$^{B27}$ human insulin,
Ala$^{A21}$,Arg$^{B27}$ human insulin,
His$^{A21}$,Arg$^{B27}$ human insulin,
Asp$^{A21}$,Arg$^{B27}$,Lys$^{B30}$—NH$_2$ human insulin,
Asp$^{A21}$,Arg$^{B27}$ human insulin,
Gly$^{A21}$,Arg$^{B27}$ human insulin,
Gln$^{A17}$,Ser$^{A21}$,Arg$^{B27}$ human insulin,
Gln$^{A17}$,Thr$^{A21}$,Arg$^{B27}$ human insulin,
Gln$^{A17}$,Ala$^{A21}$,Arg$^{B27}$ human insulin,
Gln$^{A17}$,His$^{A21}$,Arg$^{B27}$ human insulin,
Gln$^{A17}$,Asp$^{A21}$,Arg$^{B27}$ human insulin,
Gln$^{A17}$,Gly$^{A21}$,Arg$^{B27}$ human insulin,
Gln$^{A17}$,Ser$^{A21}$,Gln$^{B13}$ human insulin,
Gln$^{A17}$,Thr$^{A21}$,Gln$^{B13}$ human insulin,
Gln$^{A17}$,Ala$^{A21}$,Gln$^{B13}$ human insulin,
Gln$^{A17}$,His$^{A21}$,Gln$^{B13}$ human insulin,
Gln$^{A17}$,Asp$^{A21}$,Gln$^{B13}$ human insulin,
Gln$^{A17}$,Gly$^{A21}$,Gln$^{B13}$ human insulin,
Arg$^{B27}$,Ser$^{A21}$,Gln$^{B13}$ human insulin,
Arg$^{B27}$,Thr$^{A21}$,Gln$^{B13}$ human insulin,
Arg$^{B27}$,Ala$^{A21}$,Gln$^{B13}$ human insulin,
Arg$^{B27}$,His$^{A21}$,Gln$^{B13}$ human insulin,
Arg$^{B27}$,Asp$^{A21}$,Gln$^{B13}$ human insulin,
Arg$^{B27}$,Gly$^{A21}$,Gln$^{B13}$ human insulin,
Gln$^{A17}$,Ser$^{A21}$,Lys$^{B27}$ human insulin,
Gln$^{A17}$,Thr$^{A21}$,Lys$^{B27}$ human insulin,
Gln$^{A17}$,Ala$^{A21}$,Lys$^{B27}$ human insulin,
Gln$^{A17}$,His$^{A21}$,Lys$^{B27}$ human insulin,
Gln$^{A17}$,Asp$^{A21}$,Lys$^{B27}$ human insulin,
Gln$^{A17}$,Gly$^{A21}$,Lys$^{B27}$ human insulin,
Gln$^{B13}$,Ser$^{A21}$,Lys$^{B27}$ human insulin,
Gln$^{B13}$,Thr$^{A21}$,Lys$^{B27}$ human insulin,
Gln$^{B13}$,Ala$^{A21}$,Lys$^{B27}$ human insulin,
Gln$^{B13}$,His$^{A21}$,Lys$^{B27}$ human insulin,
Gln$^{B13}$,Asp$^{A21}$,Lys$^{B27}$ human insulin,
Gln$^{B13}$,Gly$^{A21}$,Lys$^{B27}$ human insulin,
hSer$^{A21}$,Arg$^{B27}$,Thr$^{B30}$—NH$_2$ human insulin
at a pH value of 2.5–5.8 and containing therein zinc ions in a concentration from 5 μu to 200 μg zinc per ml.

6. A human insulin analog having an amino acid residue at A21, selected from the group consisting of Glu, Asp, Lys, Arg, His, Val, Gln, Ile, Phe, Tyr, Met, Gly, Ser, Thr, Ala, Leu, Trp and hSer, wherein at least one of the amino acid residues at A4, A17, B13, and B21 is a neutral amino acid residue selected from the group consisting of Gly, Val, Ile, Leu, Phe, Tyr, Met, Asn, Gln, Ala, Ser and Thr, and wherein the C-terminal carboxyl group of the B-chain is amidated with the proviso that the insulin analog has at least one charge more than human insulin at a pH value of 7.

7. A human insulin analog having an amino acid residue at A21, selected from the group consisting of Glu, Asp, Lys, Arg, His, Val, Gln, Ile, Phe, Tyr, Met, Gly, Ser, Thr, Ala, Leu, Trp and hSer, wherein at least one of the amino acid residues at A4, A17, B13, and B21 is a neutral amino acid residue selected from the group consisting of Gly, Val, Ile, Leu, Phe, Tyr, Met, Asn, Gln, Ala, Ser and Thr, and wherein the B27 amino acid residue is Lys or Arg with the proviso that the insulin analog has at least one charge more than human insulin at a pH value of 7.

8. A human insulin analog having an amino acid residue at A21, selected from the group consisting of Glu, Asp, Lys, Arg, His, Val, Gln, Ile, Phe, Tyr, Met, Gly, Ser, Thr, Ala, Leu, Trp and hSer, wherein the B27 amino acid residue is Lys or Arg and wherein the C-terminal carboxyl group of the B-chain is amidated with the proviso that the insulin analog has at least one charge more than human insulin at a pH value of 7.

9. A human insulin analog having an amino acid residue at A21, selected from the group consisting of Glu, Asp, Lys, Arg, His, Val, Gln, Ile, Phe, Tyr, Met, Gly, Ser, Thr, Ala, Leu, Trp and hSer, wherein at least one of the amino acid residues at A4, A17, B13, and B21 is a neutral amino acid residue selected from the group consisting of Gly, Val, Ile, Leu, Phe, Tyr, Met, Asn, Gln, Ala, Ser and Thr, wherein the B27 amino acid residue is Lys or Arg and wherein the C-terminal carboxyl group of the B-chain is amidated with the proviso that the insulin analog has at least one charge more than human insulin at a pH value of 7.

10. An aqueous solution of a human insulin analog having an amino acid residue at A21, selected from the group consisting of Glu, Asp, Lys, Arg, His, Val, Gln, Ile, Phe, Tyr, Met, Gly, Ser, Thr, Ala, Leu, Trp and hSer, wherein at least one of the amino acid residues at A4, A17, B13, and B21 is a neutral amino acid reside selected from the group consisting of Gly, Val, Ile, Leu, Phe, Tyr, Met, Asn, Gln, Ala, Ser and Thr, wherein the B27 amino acid residue is Lys or Arg and wherein the C-terminal carboxyl group of the B-chain is amidated at a pH value of 2.5–5.8 and containing therein zinc ions in a concentration from 5 µg to 200 µg zinc per ml with the proviso that the insulin analog has at least one charge more than human insulin at a pH value of 7.

* * * * *